United States Patent
Grunstad et al.

(10) Patent No.: US 8,534,328 B2
(45) Date of Patent: Sep. 17, 2013

(54) ADAPTERS FOR USE WITH AN ANESTHETIC VAPORIZER

(75) Inventors: Jerome A. Grunstad, Inver Grove Heights, MN (US); David A. Schuelke, Hudson, WI (US); Paul L. Weber, Hudson, WI (US); Martin E. Olson Gunderson, River Falls, WI (US); Simon Freed, Hillsborough, NJ (US)

(73) Assignees: Baxter International Inc., Deerfield, IL (US); Baxter Healthcare SA, Glattpark (Opifkon) (CH)

( * ) Notice: Subject to any disclaimer, the term of this patent is extended or adjusted under 35 U.S.C. 154(b) by 1529 days.

(21) Appl. No.: 12/100,019

(22) Filed: Apr. 9, 2008

(65) Prior Publication Data

US 2009/0255532 A1 Oct. 15, 2009

(51) Int. Cl.
*B65B 1/04* (2006.01)
*B60K 15/04* (2006.01)

(52) U.S. Cl.
CPC .................................. *B60K 15/04* (2013.01)
USPC ............ 141/368; 141/301; 141/346; 141/347

(58) Field of Classification Search
USPC ................. 141/117, 286, 301, 302, 346–347, 141/350, 351, 368, 392
See application file for complete search history.

(56) References Cited

U.S. PATENT DOCUMENTS

| | | | |
|---|---|---|---|
| 2,324,793 A * | 7/1943 | Minard | 141/58 |
| 2,711,279 A * | 6/1955 | Day et al. | 141/55 |
| 2,716,517 A * | 8/1955 | Tollberg | 141/117 |
| 3,416,577 A * | 12/1968 | Franz | 141/117 |
| 3,848,645 A * | 11/1974 | Franz | 141/117 |
| 3,871,425 A * | 3/1975 | Fee et al. | 141/5 |
| 4,625,779 A | 12/1986 | Ryschka et al. | |
| 4,693,853 A | 9/1987 | Falb et al. | |
| 4,825,860 A | 5/1989 | Falb et al. | |
| 4,862,918 A | 9/1989 | Schroeder | |
| 4,867,212 A | 9/1989 | Mohr et al. | |
| 4,879,997 A | 11/1989 | Bickford | |
| 4,883,049 A | 11/1989 | McDonald et al. | |
| 4,893,659 A | 1/1990 | Loliger et al. | |
| 4,932,398 A | 6/1990 | Lancaster et al. | |
| 5,048,874 A | 9/1991 | Ohlsson et al. | |

(Continued)

FOREIGN PATENT DOCUMENTS

| | | |
|---|---|---|
| DE | 102004043652 | 10/2005 |
| EP | 0 678 042 | 10/1995 |

(Continued)

OTHER PUBLICATIONS

Invitation to Pay Additional Fees and Communication Relating to the Results of the Partial International Search (Jul. 7, 2009) (5 pages).

(Continued)

*Primary Examiner* — Timothy L Maust
(74) *Attorney, Agent, or Firm* — Marshall, Gerstein & Borun LLP

(57) ABSTRACT

Adapters are provided for establishing fluid communication between an anesthetic agent container and an anesthetic vaporizer having a fluid port. The adapter may be mountable on the vaporizer to cooperate with the spout of an anesthetic agent container or may be mountable on an anesthetic agent container to cooperate with the fluid port of an anesthetic vaporizer to provide a sealing and/or retaining relationship therebetween.

5 Claims, 14 Drawing Sheets

(56) References Cited

U.S. PATENT DOCUMENTS

| | | | |
|---|---|---|---|
| 5,144,984 A | 9/1992 | Westerberg et al. |
| 5,144,991 A | 9/1992 | Wallroth et al. |
| 5,170,823 A | 12/1992 | Gregory et al. |
| 5,287,898 A | 2/1994 | Falb et al. |
| 5,301,723 A * | 4/1994 | Goode ............................ 141/82 |
| 5,381,836 A | 1/1995 | Braatz et al. |
| 5,419,316 A | 5/1995 | Bernstein |
| 5,427,145 A | 6/1995 | Grabenkort |
| 5,474,112 A | 12/1995 | Carola et al. |
| 5,478,506 A | 12/1995 | Lavimodiere et al. |
| 5,505,236 A | 4/1996 | Grabenkort et al. |
| 5,536,047 A | 7/1996 | Detable et al. |
| 5,585,045 A | 12/1996 | Heinonen et al. |
| 5,617,906 A | 4/1997 | Braatz et al. |
| 5,653,475 A | 8/1997 | Scheyhing et al. |
| 5,682,874 A | 11/1997 | Grabenkort et al. |
| 5,687,777 A | 11/1997 | Dobson et al. |
| 5,740,835 A | 4/1998 | Murphy |
| 5,758,640 A | 6/1998 | Kamppari et al. |
| 5,799,711 A | 9/1998 | Heinonen et al. |
| 5,810,001 A | 9/1998 | Genga et al. |
| 5,839,487 A | 11/1998 | Moll et al. |
| 5,860,502 A | 1/1999 | Grosspietsch et al. |
| 5,911,250 A | 6/1999 | Turker et al. |
| 5,915,427 A | 6/1999 | Grabenkort |
| 5,983,964 A | 11/1999 | Zielinksi et al. |
| 6,125,893 A | 10/2000 | Braatz et al. |
| 6,138,672 A | 10/2000 | Kankkunen |
| 6,149,206 A | 11/2000 | DiRocco |
| 6,231,084 B1 | 5/2001 | Hester et al. |
| 6,371,528 B1 | 4/2002 | Kimura et al. |
| 6,394,087 B1 | 5/2002 | Kankkunen et al. |
| 6,484,765 B1 * | 11/2002 | Clemmons et al. ........... 141/292 |
| 6,585,016 B1 | 7/2003 | Falligant et al. |
| 6,637,725 B2 | 10/2003 | Davis et al. |
| 6,672,306 B2 | 1/2004 | Loser et al. |
| 6,676,172 B2 | 1/2004 | Alksnis et al. |
| 6,745,765 B2 | 6/2004 | Kullik et al. |
| 6,745,800 B1 | 6/2004 | Sansom et al. |
| 6,789,698 B2 | 9/2004 | Gloor et al. |
| 6,817,390 B2 | 11/2004 | Falligant et al. |
| 6,929,041 B2 | 8/2005 | Falligant et al. |
| 6,948,642 B2 | 9/2005 | Awad |
| 7,168,467 B2 | 1/2007 | Turker et al. |
| 7,290,571 B2 | 11/2007 | Bunke et al. |
| 7,389,801 B2 | 6/2008 | Turker et al. |
| 7,472,700 B2 | 1/2009 | Gershteyn |
| 7,546,856 B2 | 6/2009 | Chotenovsky |
| 2003/0075241 A1 | 4/2003 | Videbrink |
| 2004/0206417 A1 | 10/2004 | Falligant et al. |
| 2005/0145296 A1 | 7/2005 | Burr |
| 2006/0048842 A1 | 3/2006 | Bunke et al. |
| 2007/0204931 A1 | 9/2007 | Freed et al. |
| 2007/0204932 A1 | 9/2007 | Freed et al. |
| 2008/0308179 A1 | 12/2008 | Danielsen |
| 2008/0319422 A1 | 12/2008 | Cardenas |
| 2009/0255532 A1 | 10/2009 | Grunstad et al. |
| 2009/0260627 A1 | 10/2009 | Cuzydlo et al. |
| 2010/0018528 A1 | 1/2010 | Cuzydlo |
| 2010/0018607 A1 | 1/2010 | Cuzydlo |

FOREIGN PATENT DOCUMENTS

| | | |
|---|---|---|
| WO | WO 95/26772 | 10/1995 |
| WO | WO 96/06301 | 2/1996 |
| WO | WO 2008/048947 | 4/2008 |
| WO | WO 2010/002658 | 1/2010 |

OTHER PUBLICATIONS

International Search Report and Written Opinion from counterpart International Application No. PCT/US09/39302, Oct. 20, 2009 (16 pages).

* cited by examiner

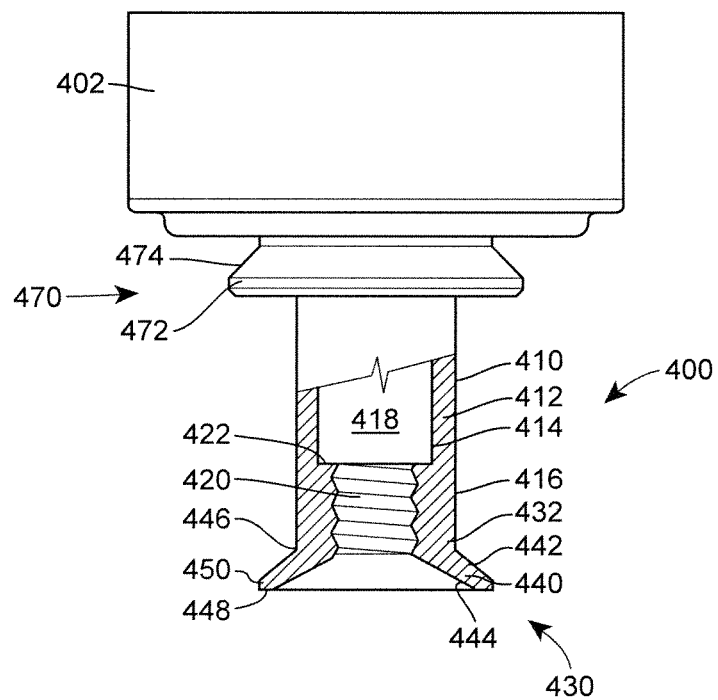

ADAPTERS FOR USE WITH AN ANESTHETIC VAPORIZER

BACKGROUND

This patent is directed to an adapter for use with an anesthetic vaporizer, and, in particular, to an adapter to be coupled to an anesthetic agent container or a vaporizer fluid port so as to be used with an anesthetic vaporizer.

During surgical procedures, it often is necessary to anesthetize a patient. One method of delivering anesthetic is in a gaseous form, which is inhaled by the patient. For the safety of the patient and medical personnel, the anesthetic agent is typically transported in liquid form in a suitable container. Known liquid anesthetics include halothane, isoflurane, sevoflurane, desflurane, enflurane, and methoxyflurane. The liquid anesthetic is ultimately dispensed into an anesthetic vaporizer, which mixes the liquid anesthetic agent with a carrier gas, such as oxygen or nitrous oxide, that is inhalable by a patient.

Liquid anesthetics are relatively volatile and can evaporate at room temperature. Before it can be used, the anesthetic agent must be transferred from a first closed environment, e.g., a container or vial, to a second closed environment, e.g., a vaporizer. In order to transfer the anesthetic, it is well-known to provide a vaporizer fluid port with a valving system that is selectively openable to allow a liquid anesthetic agent to be poured into an internal sump of the vaporizer.

U.S. Pat. Nos. 5,381,836 and 5,617,906 to Braatz et al., which are hereby incorporated herein by reference, disclose certain valving systems for use with anesthetic vaporizers. The valving systems described in Braatz et al. may be suitable for use with, for example, commercial desflurane vaporizers. Examples of such commercial vaporizers may include, but are not limited to, the Tec 6 Plus™ of Datex-Ohmeda, Inc. and the D-Vapor™ or Devapor® of Draeger Medical AG & Co. KG.

The filling systems of Braatz et al. disclose a tubular spout that is in fluid communication with a fluid port of the vaporizer. The tubular spout has a free end that is encircled by an elastomeric o-ring seated in a groove or channel of the spout. The o-ring deforms to limit exhaust of fluids from the spout and/or associated fluid port of the vaporizer.

As set forth in more detail below, the present disclosure sets forth an improved adapter embodying advantageous alternatives to the sealing and/or retention systems of prior art devices.

SUMMARY OF THE INVENTION

In one aspect, an adapter is provided for establishing fluid communication between an anesthetic agent container and an anesthetic vaporizer. The adapter is used with a fluid port having first and second ends, a stem-like post disposed at the first end of the fluid port with a passage therethrough and a plurality of openings disposed about the post. The adapter includes a conduit having a passage sized to accept the stem-like post of the fluid port, a side wall disposed about the conduit and having an upper edge, and a bottom wall coupling the conduit and the side wall, the bottom wall having a plurality of openings disposed about the conduit to be aligned with the plurality of openings of the fluid port. The adapter also includes a seal disposed on the upper end of the side wall, and a fastener to be disposed in the passage of the conduit and the passage of the stem-like post of the fluid port, the fastener having a passage therethrough.

In another aspect, an adapter includes a spout having an internal passage therethrough for receiving a stem-like conduit, and an external surface, and a seal coupled to the external surface. The seal includes at least one annular projection integrally formed with and joined to the external surface of the spout, the at least one annular projection being disposed encircling the spout.

In still another aspect, an adapter includes a spout having an internal passage therethrough for receiving a stem-like conduit and an external surface. The spout has a recess defined in the external surface of the spout, and a seal disposed in the recess to encircle the spout. The seal includes a sealing member having a base with a base length in the longitudinal direction, and a projection with a projection length in the longitudinal direction that is significantly smaller than the base length, the projection integrally formed with and joined to the base at its midsection.

In a further aspect, an adapter includes a spout having an internal passage therethrough for receiving a stem-like conduit, and an external surface, the external surface having a first recess and a second recess formed therein, the first and second recesses spaced from each other. The adapter also includes a seal comprising a seal wall having a first end and a second end, the first end of the seal wall disposed in the first recess and the second end of the seal wall disposed in the second recess.

In a still further aspect, an adapter includes a spout having an internal passage therethrough for receiving a stem-like conduit, and an external surface, and a seal comprising a sleeve, the sleeve having a sleeve internal surface disposed about the external surface of the spout and a sleeve external surface that defines a plurality of protrusions, each protrusion encircling the spout. The sleeve has a first end and a second end, the sleeve internal surface secured to the external surface of the spout at least partially over its surface.

In an additional aspect, an adapter includes a spout having an internal passage therethrough for receiving a stem-like conduit, and an external surface, the spout having a first end and a second end. The adapter also includes a seal comprising a sleeve, the sleeve having a sleeve internal surface disposed about the external surface of the spout. The sleeve has a first end and a second end coupled to the external surface of the spout, the first end depending a first distance longitudinally beyond the first end of the spout in a first, disengaged state, and the first end depending a second distance smaller than the first distance longitudinally beyond the first end of the spout in a second, engaged state, the sleeve internal surface spaced in part from the external surface of the spout in the engaged state.

In a further additional aspect, an adapter assembly is provided for a vaporizer fluid port assembly. The vaporizer fluid port assembly has an elongated slot with a first end into which an anesthetic container spout may be advanced or withdrawn and a second end in which the motion of the spout towards or away from the slot is limited and a plate disposed over the slot. The adapter assembly includes a conduit disposed through the aperture in the plate, the conduit attached to the plate to limit the movement of the adapter assembly relative to the plate and a seal attached to the conduit. The conduit is disposed in a fluid port of the vaporizer fluid port assembly to dispose the seal at a particular location within the fluid port.

Additional aspects of the disclosure are defined by the claims of this patent.

BRIEF DESCRIPTION OF THE DRAWINGS

It is believed that the disclosure will be more fully understood from the following description taken in conjunction with the accompanying drawings. Some of the figures may have been simplified by the omission of selected elements for the purpose of more clearly showing other elements. Such omissions of elements in some figures are not necessarily indicative of the presence or absence of particular elements in any of the exemplary embodiments, except as may be explicitly delineated in the corresponding written description. None of the drawings are necessarily to scale.

FIG. 4 is a cross-sectional view of an adapter attached to a container spout;

FIG. 5 is a cross-sectional view of the adapter of FIG. 4 in combination with a vaporizer fluid port;

DETAILED DESCRIPTION OF VARIOUS EMBODIMENTS

Although the following text sets forth a detailed description of different embodiments of the invention, it should be understood that the legal scope of the invention is defined by the words of the claims set forth at the end of this patent. The detailed description is to be construed as exemplary only and does not describe every possible embodiment of the invention since describing every possible embodiment would be impractical, if not impossible. Numerous alternative embodiments could be implemented, using either current technology or technology developed after the filing date of this patent, which would still fall within the scope of the claims defining the invention.

It should also be understood that, unless a term is expressly defined in this patent using the sentence "As used herein, the term '_____' is hereby defined to mean . . ." or a similar sentence, there is no intent to limit the meaning of that term, either expressly or by implication, beyond its plain or ordinary meaning, and such term should not be interpreted to be limited in scope based on any statement made in any section of this patent (other than the language of the claims). To the extent that any term recited in the claims at the end of this patent is referred to in this patent in a manner consistent with a single meaning, that is done for sake of clarity only so as to not confuse the reader, and it is not intended that such claim term be limited, by implication or otherwise, to that single meaning. Finally, unless a claim element is defined by reciting the word "means" and a function without the recital of any structure, it is not intended that the scope of any claim element be interpreted based on the application of 35 U.S.C. §112, sixth paragraph.

Figure 1A:
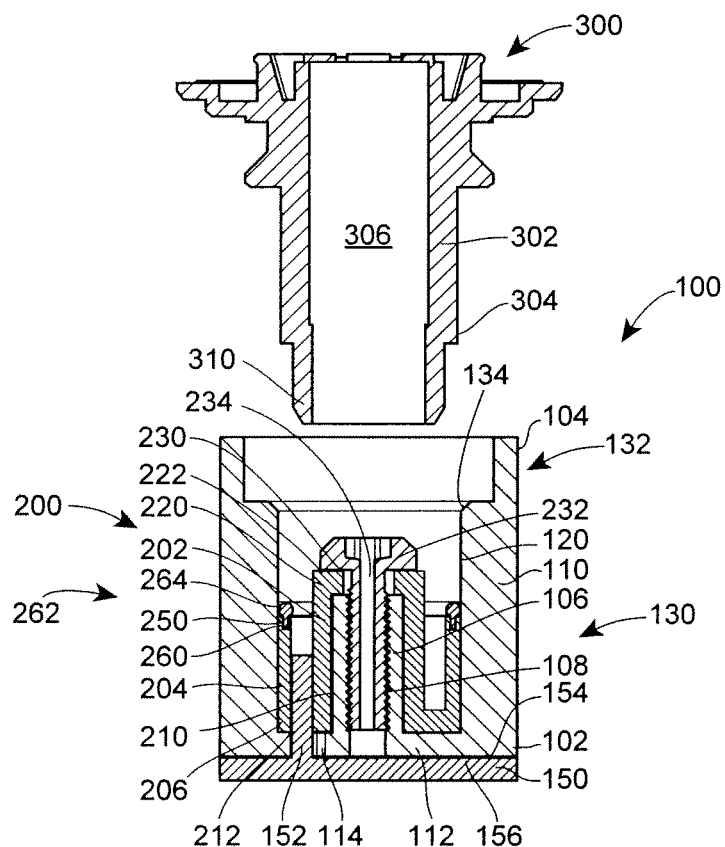
FIG. 1A is a cross-sectional view of a system including a vaporizer fluid port, an adapter, and a container spout, with the spout disengaged from the port.

Referring first to FIGS. 1A, vaporizer fluid port 100 is illustrated, such is used with the D-Vapor™ vaporizer unit of Draeger Medical AG & Co. KG. Fluid port 100 has first and second ends 102, 104. Disposed at first end 102 of the fluid port 100 is stem-like post 106 with passage 108 therethrough. Disposed about post 106 is side wall 110. Post 106 and side wall 110 are connected by bottom wall 112. Bottom wall 112 has openings 114 disposed therethrough. It will be recognized that although wall 110 has been referred to as side wall 110, and that although wall 112 has been referred to as bottom wall 112, the use of adjectives such as "side" and "bottom" are for ease of explanation, and are not intended to limit the embodiment to any particular orientation.

Side wall 110 has stepped surface 120 that defines first region 130 with a first diameter and second region 132 with a second diameter different than the first diameter. The stepped surface 120 changes abruptly to define shoulder 134 between first region 130 and second region 132.

Figure 1B:
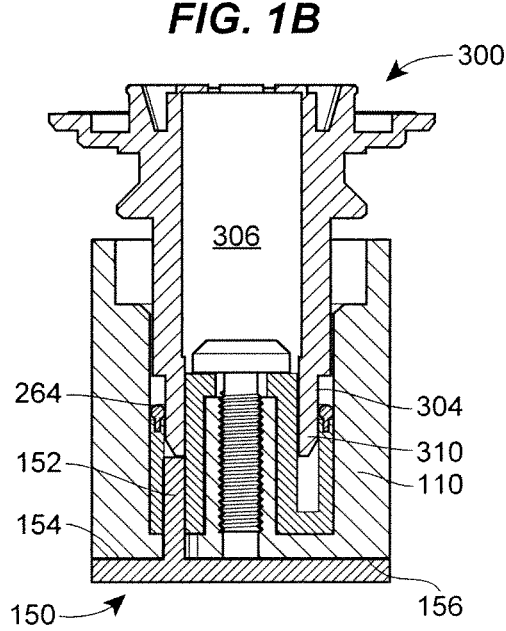
FIG. 1B is a cross-sectional view of the system of FIG. 1A, with the spout partially engaged in the port.
Figure 1C:
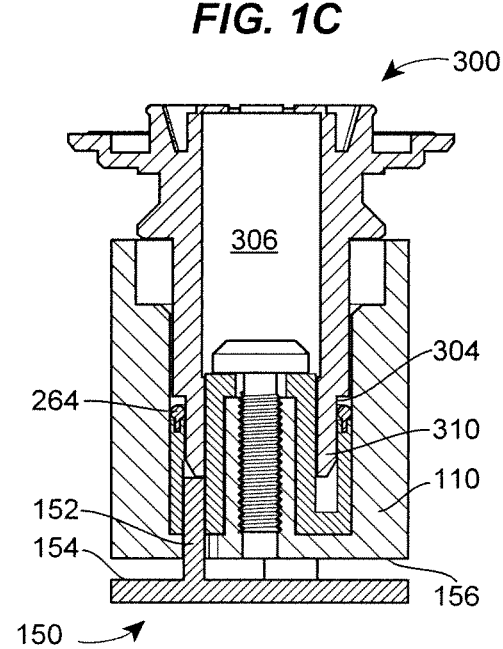
FIG. 1C is a cross-sectional view of the system of FIG. 1A, with the spout fully engaged in the port.
Figure 2:
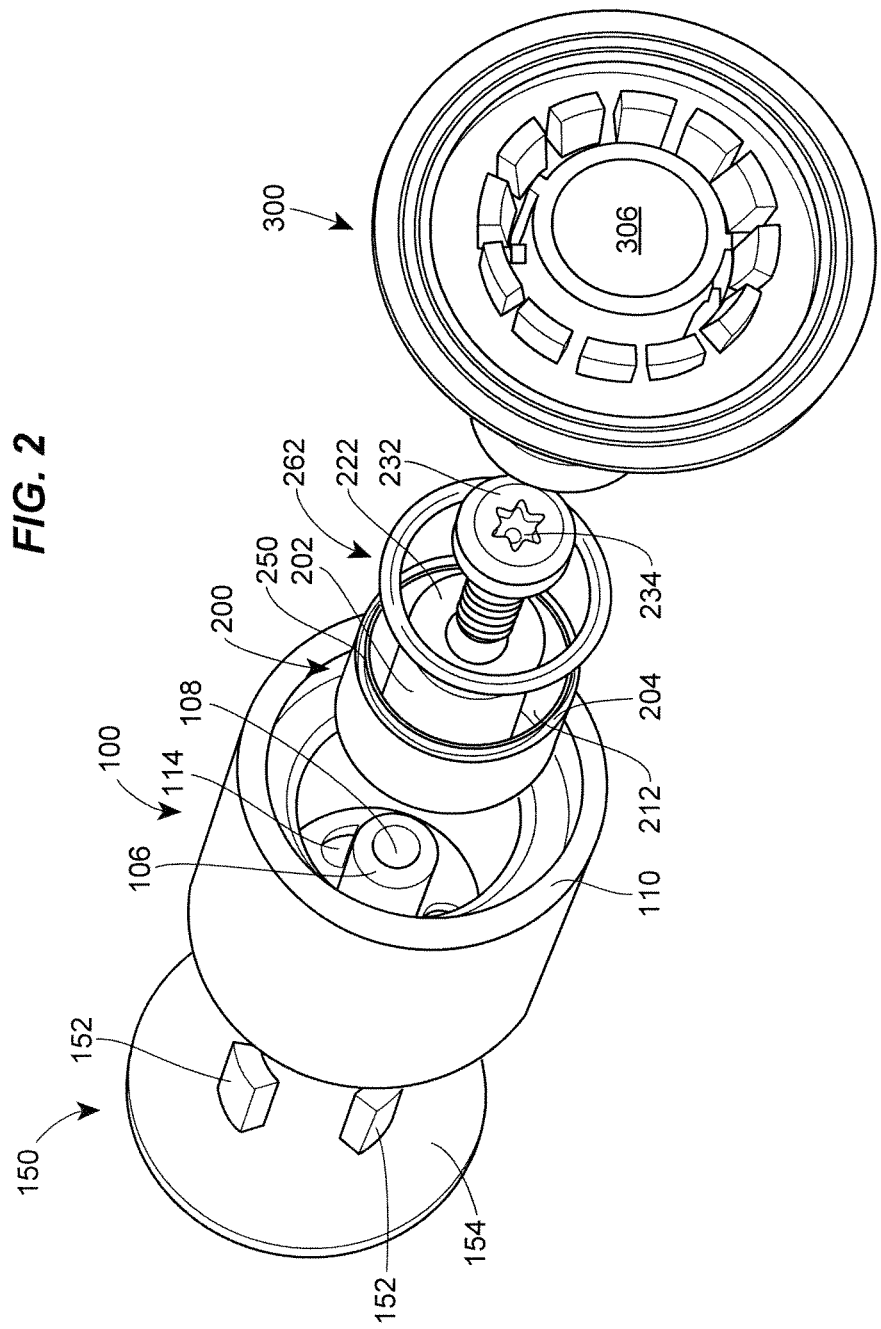
FIG. 2 is an exploded, perspective view of the system of FIG. 1A as viewed from the front.
Figure 3:
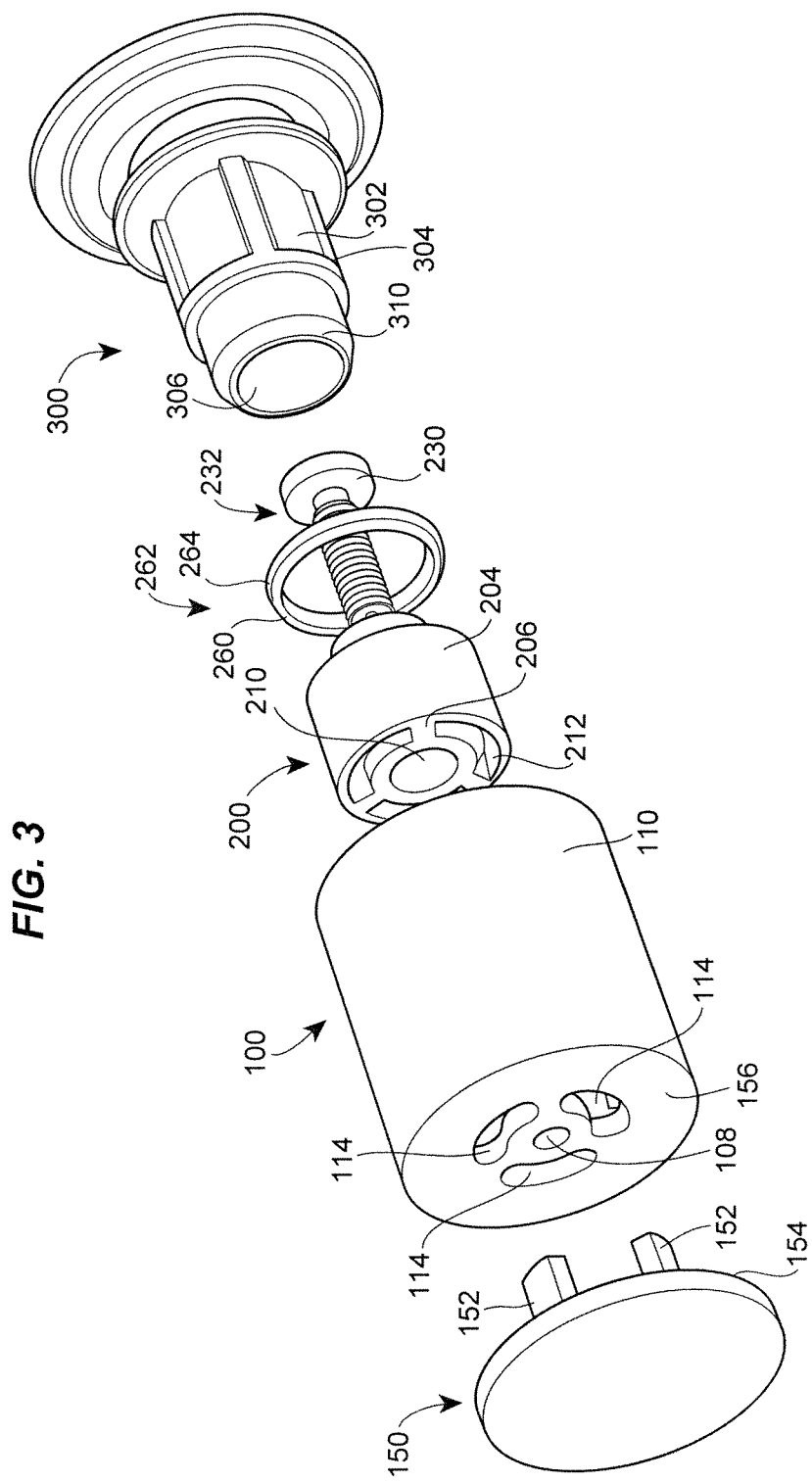
FIG. 3 is an exploded, perspective view of the system of FIG. 1A as viewed from the rear.

As mentioned above, openings 114 are disposed at first end 102 of the port 100. Plate 150 is disposed adjacent openings 114. Plate 150 has posts 152 depending from surface 154 of the plate 150, surface 154 facing surface 156 of port 100. Posts 152 depend into openings 114 to guide the movement of plate 150 relative to port 100. In particular, plate 150 is moveable between a closed state, such as is illustrated in FIGS. 1A and 1B, with surfaces 154, 156 abutting or in close proximity to each other, and an open state, such as is illustrated in FIG. 1C, with surfaces 154, 156 spaced from each other.

Adapter 200 is disposed in a space defined by post 106, side wall 110, and bottom wall 112. As illustrated, adapter 200 includes inner tubular conduit 202 and outer wall 204, which wall 204 may be concentric with inner tubular conduit 202. Bottom wall 206 depends between inner conduit 202 and outer wall 204. Here again, the used of "side" and "bottom" are for ease of explanation and comparison with the port 100, and are not intended to limit the embodiment to a particular orientation, as will be true of other terms used below.

Conduit 202 has passage 210 to receive post 106. As illustrated, the diameter of passage 210 may be the same or slightly larger than the diameter of post 106. Wall 204 has a diameter that may be the same as or slightly smaller than the diameter of region 130. Further, bottom wall 206 may have openings 212 that are sized to be substantially equal in size to openings 114, such that openings 212 may be aligned with openings 114 to receive posts 152 therethrough.

Conduit 202 may have shoulder 220 at an end of conduit 202. Shoulder 220 may abut an end of post 106 with adapter 200 disposed in the space defined by post 106, side wall 110 and bottom wall 112; according to other embodiments, shoulder 220 may be omitted, or shoulder 220 may be spaced from post 106. Surface 222 of conduit 202 faces surface 230 of fastener 232 with fastener 232 received in passage 108 in post 106. Cooperation of surfaces 222, 230 limits movement of adapter 200 relative to port 100.

Passage 108 is sized to receive fastener 232. Because fastener 232 is a threaded fastener, passage 108 may be at least partially threaded to engage threaded fastener 232. However, it will be recognized that passage 108 need not be threaded according to an embodiment wherein fastener 232 is not itself threaded. Fastener 232 has passage 234 that permits fluid flow through fastener 232.

Adapter 200 has groove 250 formed in an end of wall 204. Groove 250 is sized to receive first portion 260 of seal 262. As illustrated, groove 250 has a substantially rectangular cross-section, and first portion 260 of seal 262 has a complementary substantially rectangular cross-section, with the dimensions of portion 260 being equal to or slightly smaller than that of groove 250. With first portion 260 received within groove 250, seal 262 is coupled to adapter 200. According one embodiment of the present disclosure, seal 262 is integrally-molded with the adapter 200.

Second portion 264 of seal 262 is substantially circular in cross-section. While a circular geometry is illustrated, other geometries may be used. Portion 264 of seal 262 may be spaced from the side wall 110 or may abut side wall 110. As illustrated in FIG. 1A, portion 264 abuts side wall 110.

Spout 300 is also illustrated in FIGS. 1A-C, 2 and 3. As noted above, spout 300 may be coupled to a container of liquid anesthetic. Spout 300 includes a wall 302, with outer surface 304 and inner passage 306. Liquid anesthetic passes along passage 306, around the exterior of post 106/conduit 202 and through openings 114, 212 and into the vaporizer, while gaseous anesthetic passes through passage 108 in the post 106 and passage 234 of fastener 232 into the container via a valve assembly (not shown). Outer surface 304 cooperates with second portion 264 of seal 262 to limit passage of liquid anesthetic out of second end 104 of port 100. For example, surface 304 may abut second portion 264, or surface 304 may abut second portion 264 and cause second portion 264 to deform between surface 304 and wall 110.

Wall 302 also has end 310, which end 310 comes in contact with posts 152 as spout 300 is advanced into port 100. As shown in FIG. 1A, with spout 300 spaced from port 100, surfaces 154, 156 abut each other and posts 152 depend through openings 114, 212. As shown in FIG. 1B, as spout 300 is advanced into port 100, end 310 abuts an end of posts 152. Further movement of spout 300 in the direction of port 100 causes force to be applied against posts 152, causing movement of plate 150. Movement of plate 150 causes spacing of surfaces 154, 156, permitting liquid anesthetic to enter the vaporizer to which port 100 is attached, and permitting gaseous anesthetic to return to the container along the passages 108, 234.

A number of additional adapters are now discussed relative to FIGS. 4-16. The adapters according to these embodiments would be used with the same type of fluid port as discussed above relative to FIGS. 1A-C, 2 and 3. However, for ease of illustration, the plate is generally omitted from the following illustrations, the operation of the vaporizer fluid port being understood from the foregoing discussion.

Unlike combination of vaporizer fluid port, adapter and container spout described above, the adapter illustrated in FIGS. 4-16 is not attached to or fitted into the vaporizer fluid port. Instead, the adapters of FIGS. 4-16 are attached to or integral with the container spout.

Adapter 400 coupled to container 402 of liquid anesthetic agent is illustrated in FIG. 4. Adapter 400 is used to establish fluid communication between container 402 and an anesthetic vaporizer, which converts the liquid anesthetic agent from container 402 into a vapor form. The vaporizer has a fluid port with a stem-like conduit and openings, as will be discussed in greater detail relative to FIG. 5.

Adapter 400 is attached to or integral with spout 410. Spout 410 has wall 412 that defines internal passage 414. A valve assembly (not shown) may be disposed within the internal passage 414, which valve assembly may be actuated by a mating portion of the fluid port of the vaporizer to permit fluid flow between the vaporizer sump and the container 402. Spout 410, or more particularly, wall 412, also has external surface 416.

Internal passage 414 may have different regions, which regions may have different surfaces, cross-sectional shapes, cross-sectional measurements (e.g., diameters), etc. As illustrated, passage 414 has at least two different regions 418, 420 that meet at shoulder 422. First region 418 has a substantially smooth surface, and a substantially circular cross-section aligned along a longitudinal axis of adapter 400. By contrast, second region 420 receives the stem-like post or conduit of the vaporizer fluid port. Second region 420 has a substantially circular cross-section aligned along the longitudinal axis of adapter 400. The diameter of first region 418 is larger than that of second region 420, and thus shoulder 422 is formed at the junction of these two regions 418, 420.

It will be recognized that a number of variations may be made to passage 414. Passage 414 may have a single, uniform shape and surface treatment along its entire length. Region 420 may have an outer surface that has a helical groove defined therein, although this need not be the case according to other embodiments, wherein region 420 could instead be smooth, although dimensioned to provide a space between the stem-like post and the region 420. Moreover, passage 414, or one of the regions thereof, may be offset relative to the longitudinal axis of adapter 400. Moreover, while a circular cross-section has been described, it is also possible to use an elliptical or other cross-sectional shape for passage 414.

External surface 416 may be substantially smooth. While other adapters, discussed below, have recesses formed into surface 416, wall 412 of adapter 400 has no recesses formed therein. Because wall 412 is annular, surface 416 is cylindrical, although that need not be the case for all embodiments of adapter 400.

Adapter 400 also includes seal 430. According to adapter 400 illustrated in FIG. 1, seal 430 is coupled to external surface 416 of wall 412 disposed encircling (i.e., continuous about the perimeter) first open end 432 of spout 410. In fact, seal 430 is defined by an annular projection integrally formed with and joined to external surface 416 of wall 412 of spout 410. Preferably, spout 410 and seal 430 are formed from high-density polyethylene (HDPE), although other materials may be used as well. Alternatively, seal 430 may be formed separately from spout 410, and still may be coupled to end 432 of spout 410 using, for example, a suitable adhesive.

Seal 430 has a tapered, annular shape. That is, seal 430 has wall 440 with external surface 442 and internal surface 444. As illustrated, external surface 442 defines a circular perimeter in cross-section, as does internal surface 444. The diameter of the circle defined by external surface 442 in cross-section generally increases between first end 446 of seal 430 and second end 448 of seal 430 spaced from the first end 446. Only over a relatively short distance, marked as 450, does external surface 442 maintain its diameter. The diameter of the circle defined by internal surface 444 in cross-section also increases between first and second ends 446, 448. Given the nature of the taper of external and internal surfaces 442, 444, the thickness of wall 440 varies between first and second ends 446, 448, although this need not be the same according to other embodiments.

Adapter 400 also includes rim 470. Rim 470 has wall 472 with tapered external surface 474 against which a locking pin may act to hold adapter 400 in position relative to the fluid port. Rim 470 is seated against the shoulder of a wall that surrounds the stem-like conduit of the vaporizer fluid port, as explained in greater detail below.

Referring now to FIG. 5, adapter 400 is now discussed in combination with fluid port 500 of anesthetic vaporizer. As mentioned above, fluid port 500 has stem-like, tubular conduit or post 502 with passage 504 defined therethrough and openings 506 in bottom wall 508. In operation, liquid anesthetic flows along passage 414 of the spout 410, between the spout 410 and the post 502, and through the openings 506, while passage 504 of conduit 502 is connected to via a valve assembly (not shown) to establish a return path for gaseous anesthetic between vaporizer and the container 402. In particular, the fluid may pass between the spout 410 and the post 502 through the grooved region 420 of the spout 410.

Disposed about conduit 502 is side wall 520. Conduit 502 and side wall 520 are connected by bottom wall 508, and define a space therebetween. Side wall 520 has stepped surface 522 that extends between ends 524, 526 of port 500. Wall 520 may extend further than is illustrated in FIG. 5, as only the portion of wall 520 that cooperates with adapter 400 and container 402 is illustrated in FIG. 5.

Stepped surface 522 depends away from first end 524. Stepped surface 522 has first region 530, having a diameter comparable to the diameter of region 450 of seal 430. This permits seal 430 to cooperate with stepped surface 522 to limit the passage of fluid out of the space defined by conduit 502, side wall 520 and bottom wall 522. According to alternative embodiments, however, seal 430 may cooperate with first end 524 of port 500 as well or in the alternative.

Stepped surface 522 tapers radially outwardly in second region 532, which region is adjacent to first region 530. In an embodiment of adapter 400 where seal 430 is sized so that region 450 has a diameter substantially similar to region 530, region 532 may assist in aligning seal 430 with region 530.

Stepped surface 522 abruptly changes diameter to define shoulder 534. Rim 470 may abut against shoulder 534 to position the rim 470 to cooperate with a locking pin (not shown). Stepped surface 522 may also define shoulder 536, against which a surface of container 402 abuts with adapter 400 in the operative position. It will be recognized that the cooperation of shoulder 436 and container 402 prevents seal 430 from cooperating with first end 524 of port 500. It will also be recognized that a further barrier may be formed between shoulder 536 and container 402, which barrier may be reinforced by disposing an O-ring, for example, between wall 520 and container 402 at shoulder 536.

Figure 6:
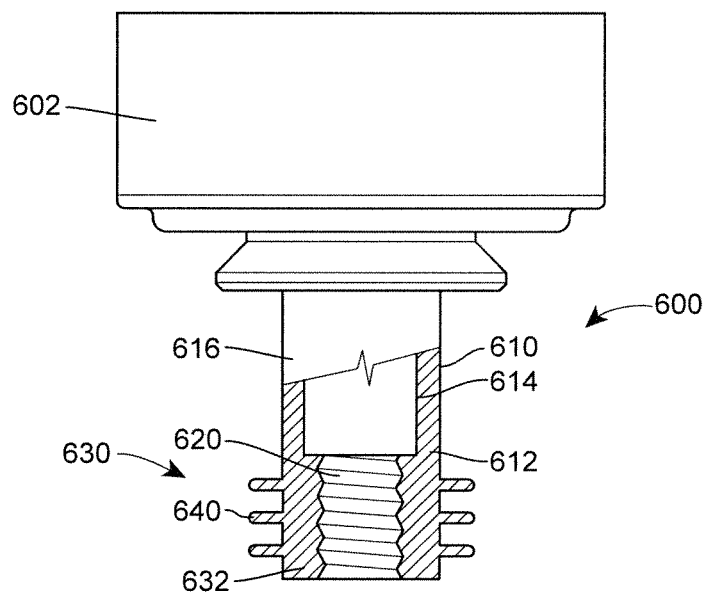
FIG. 6 is a cross-sectional view of an adapter attached to a container spout.
Figure 7:
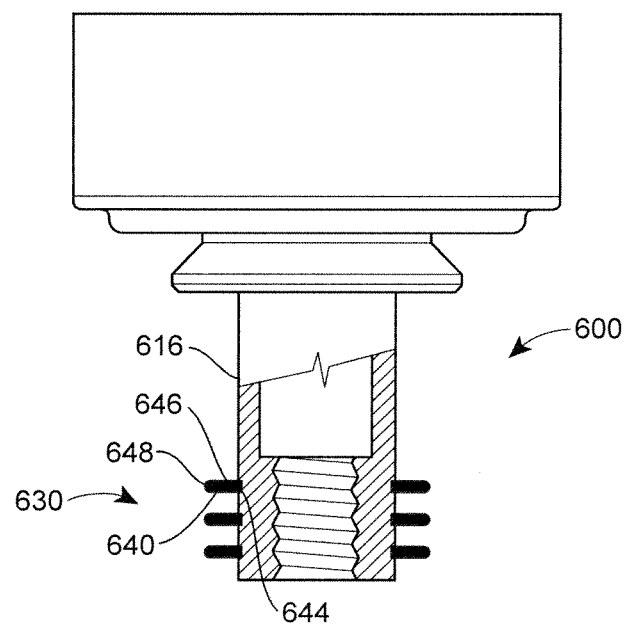
FIG. 7 is a cross-sectional view of a variant of the adapter of FIG. 6 attached to a container spout.
Figure 8:
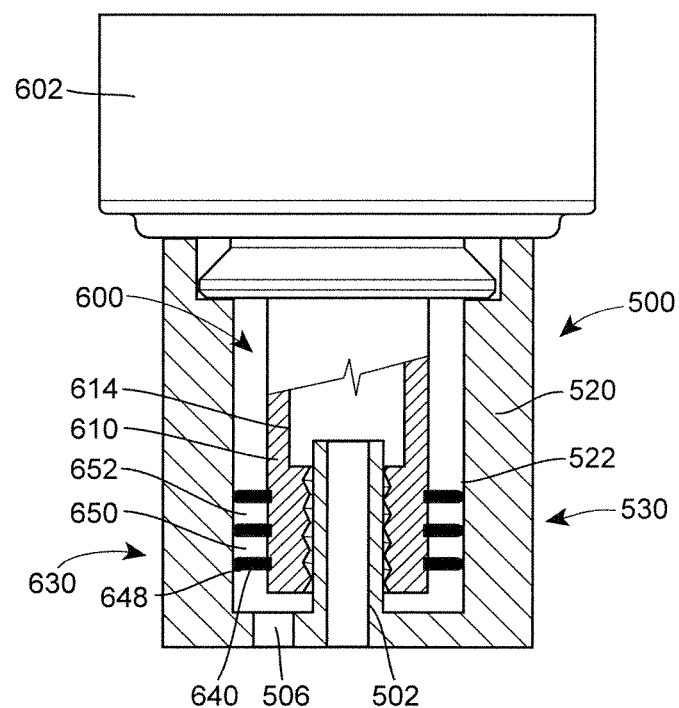
FIG. 8 is a cross-sectional view of the adapter of FIG. 7 in combination with a vaporizer fluid port.

FIGS. 6-8 illustrate another adapter 600, and a variant thereof. Adapter 600, as illustrated, shares many features in common with adapter 400, as illustrated. Adapter 600 is coupled to container 602. Adapter 600 includes spout 610 with wall 612 defining internal passage 614 and having external surface 616. Passage 614 has regions 618, 620, region 620 being grooved to define a fluid flow passage, if desired. Of course, the comments made above relative to the possible variations as to these common features would apply equally to adapter 600.

Adapter 600 differs from adapter 400 in regard to seal 630. While seal 630 is, similar to seal 430, coupled to external surface 616 of spout 610, seal 630 is not disposed at end 632 of spout 610. Instead, seal 630 depends from a region of surface 616 spaced from end 632 of spout 610.

Seal 630 includes a plurality of spaced annular projections 640, which may be referred to as fins, that depend from external surface 616 of spout 610 to encircle spout 610. According to the embodiment illustrated in FIG. 6, fins 640 are integrally formed with and joined to spout 610. According to the embodiment illustrated in FIG. 7, fins 640 are separate from spout 610, and are instead coupled to spout 610 as explained below. This permits the fins 640 from being made of a material other than that used to form the spout 610. Examples of suitable materials for fins 640 may include, but are not limited to, silicone, neoprene, and rubber (synthetic and/or natural).

To accommodate separate fins 640 of FIG. 7, surface 616 of spout 610 may have a plurality of recesses 644 formed therein. Recesses 644 may take the form of a plurality of grooves that extend about spout 610. First end 646 of fins 640 may be disposed into recesses 644, while second end 648 of fins 640 depends radially outwardly therefrom. The first ends 646 of the fins 640 may be secured within the recesses 644 with adhesive, for example. Of course, a suitable sealing mechanism will depend on the materials to be joined and other factors, but such a selection is well within the capacity of one having ordinary skill in the art.

Adapter 600, and in particular the variant of FIG. 7, is shown in FIG. 8 in context with a fluid port as was illustrated in FIG. 5. Thus, the numbering convention utilized for the fluid port in FIG. 5 will be used in regard to FIG. 8, as well as the remainder of the figures illustrating the combination of an adapter and a fluid port.

In operation, adapter 600 is disposed such that conduit 502 is in fluid communication with a valve assembly (not shown) and openings 506 are in communication with the remainder of passage 614 of spout 610. The plurality of fins 640 that define seal 630 have their second ends 648 abutting region 530 of surface 522. Seal 630 thereby defines a plurality of spaces 650, 652, and limits the passage of fluid past the seal 630.

Figure 9:
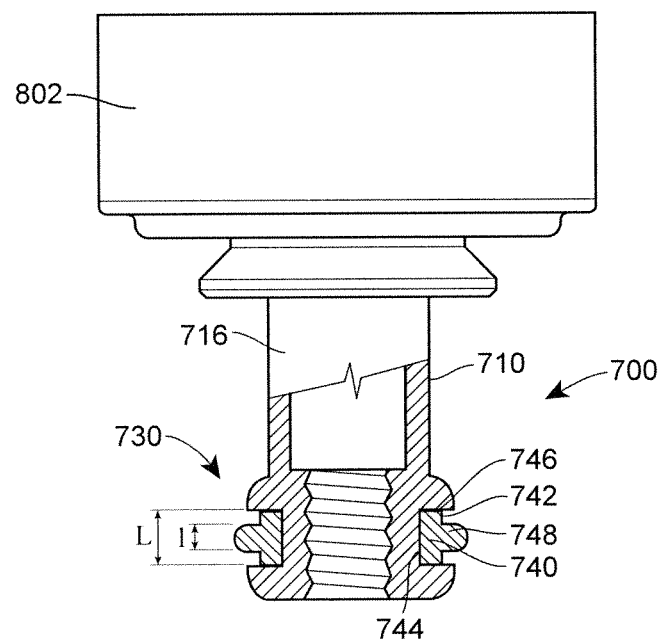
FIG. 9 is a cross-sectional view of an adapter attached to a container spout.
Figure 10:
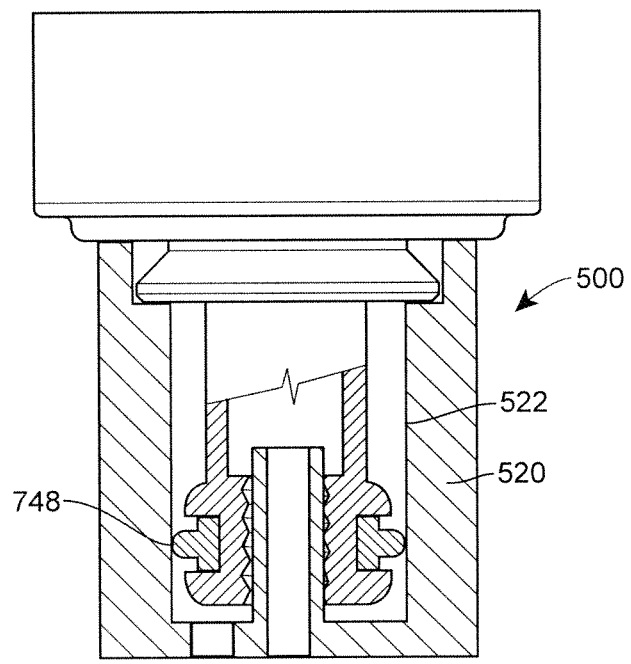
FIG. 10 is a cross-sectional view of the adapter of FIG. 9 in combination with a vaporizer fluid port.

FIGS. 9 and 10 illustrate a further adapter 700 that is similar to the variant of adapter 600 illustrated in FIG. 7 in that adapter 700 includes seal 730 that is coupled to spout 710 by having at least a part of the seal 730 received in a recess defined in external surface 716 of spout 710. This similarity may also be noted relative to adapter 800 illustrated in FIGS. 11 and 12, discussed below, in which recesses in external surface 816 of spout 810 receive portions of seal 830. Rather than repeating the similarities of the adapters, the discussion will instead focus on the differences.

Adapter 700 (as seen in FIG. 9) includes seal 730 with an annular shape to encircle spout 710. Seal 730 includes a sealing member with base 740 from which depends annular projection 742. In particular, projection 742 has first end 746 that is integrally formed with and joined to base 740 at its midsection, and second end 748 that depends radially outwardly from base 740. A length, l, in a longitudinal direction of projection 742 of seal 730 is significantly smaller than a length, L, in the longitudinal direction of base 740 of seal 730. Base 740 of seal 730 is sized to seat in recess 744 formed in exterior surface 716 of adapter 700, while second end 748 of projection 742 abuts surface 522 of wall 520 to limit passage of fluid, as seen in FIG. 10.

Figure 11:
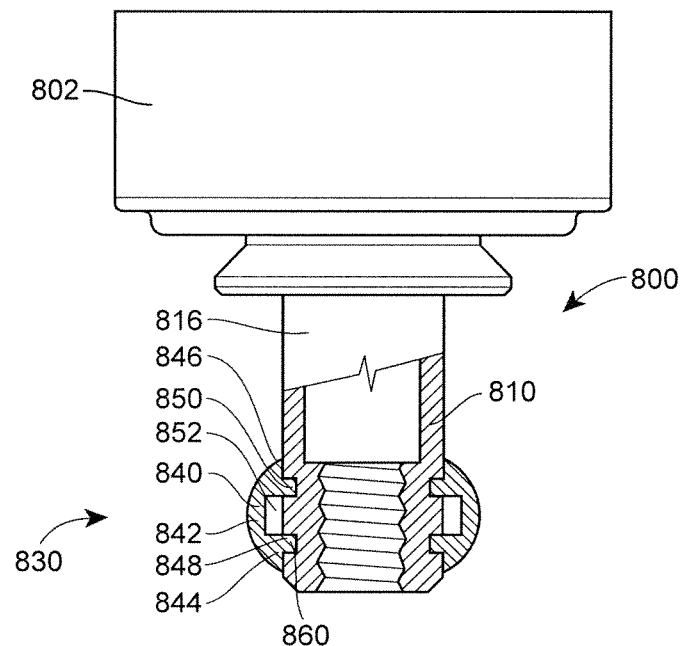
FIG. 11 is a cross-sectional view of an adapter attached to a container spout.

Adapter 800 (as seen in FIG. 11) includes seal 830 with wall 840 having a convex external surface 842, wall 840 appearing arched in cross-section. Wall 840 has first end 844 and second end 846, first and second ends 844, 846 being spaced from each other. Coupling ridges 848, 850 are coupled to each of ends 844, 846, coupling ridges 848, 850 being integrally formed with and joined to first and second ends 844, 846 of wall 840 as illustrated.

As mentioned above, adapter 800 also includes spout 810 with external surface 816 having first and second recesses 860 therein. Recesses 860 may be in the form of a pair of grooves spaced longitudinally from each other. Ridge 848 at first end 844 of seal 830 is disposed in one recess 860, while ridge 850 at second end 846 of seal 830 is disposed in the other recess 860, thereby coupling seal 830 to external surface 816 of spout 810. Additionally, an adhesive may be used to secure seal 830 to spout 810.

Figure 12:
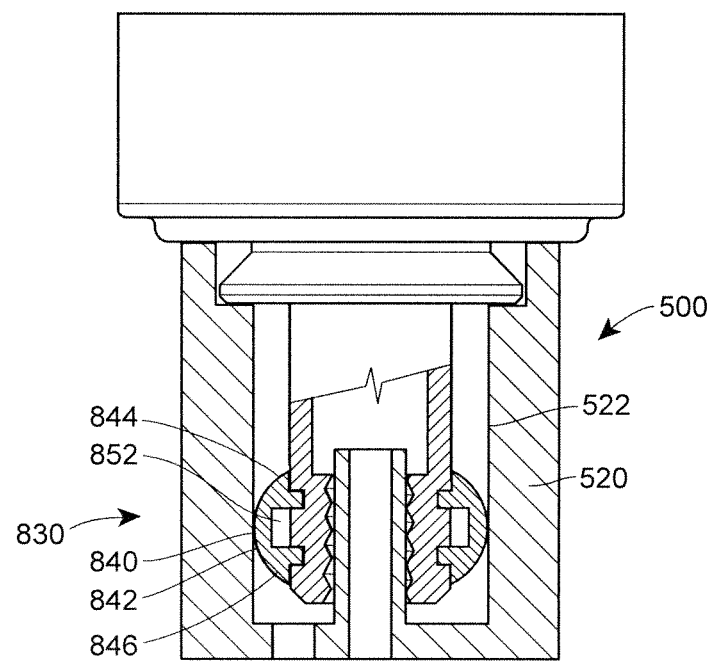
FIG. 12 is a cross-sectional view of the adapter of FIG. 11 in combination with a vaporizer fluid port.

External surface 816 of spout 810 and wall 840 define space 852. In operation, as illustrated in FIG. 12, external surface 842 of wall 840 of seal 830 abuts surface 522 of wall 520, whereby passage of fluid may be limited. It will be recognized that by providing space 852, wall 840 may deform more evenly along its length between ends 844, 846, improving the cooperation between seal 830 and surface 522 of wall 520.

FIGS. 13-16 illustrate additional embodiments of adapter 900, 1000 that include spout 910, 1010 with external surface 916, 1016 to which seal assembly 930, 1030 is attached, at least in part. However, seals 930, 1030 are not integrally formed with and joined to spouts 910, 1010, and seals 930, 1030 are not received within recesses formed in external surfaces 916, 1016 of spouts 910, 1010. Instead, seals 930, 1030 take the form of a sleeve that is disposed about spout 910, 1010, the sleeve having a dimension in the longitudinal direction that is significantly greater than a dimension in the radial direction. In this regard, the wall 840 may also be referred to as a sleeve.

Figure 13:
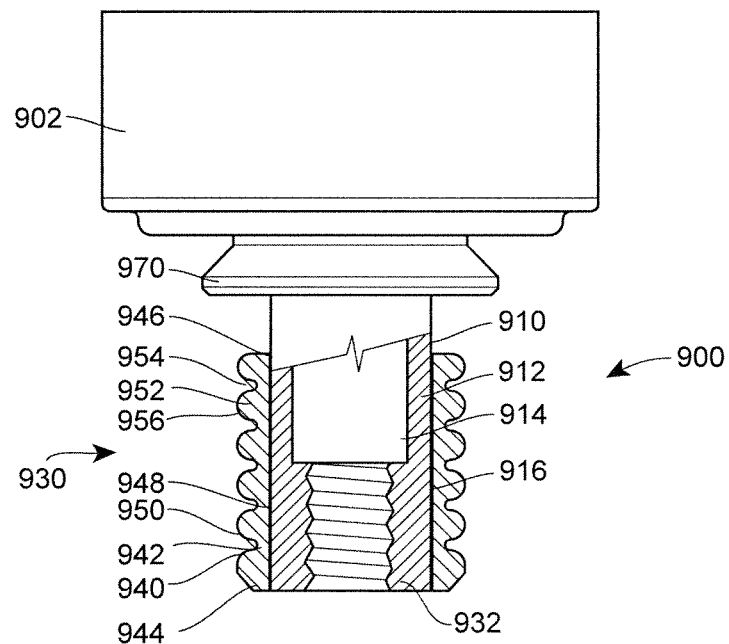
FIG. 13 is a cross-sectional view of an adapter attached to a container spout.
Figure 14:
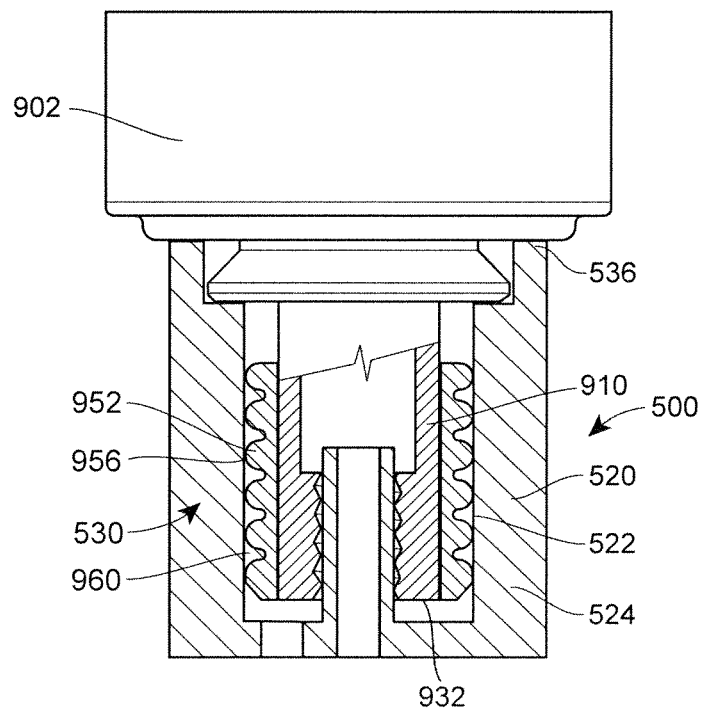
FIG. 14 is a cross-sectional view of the adapter of FIG. 13 in combination with a vaporizer fluid port.

Turning first to adapter 900, illustrated in FIGS. 13 and 14, adapter 900 includes spout 910. Spout 910 has wall 912 that defines internal passage 914 and has external surface 916. External surface 916 is uniform and cylindrical along its length. Disposed about spout 910 is seal 930, in the form of sleeve 940.

Sleeve 940 has wall 942 with first end 944 and second end 946. First end 944 of sleeve 940 is aligned with first end 932 of spout 910. Second end 946 of sleeve 940 is spaced from rim 970.

Wall 942 of sleeve 940 has internal surface 948 and external surface 950. Internal surface 948 is disposed about and secured to external surface 916 of spout 910 at least partially over its surface. According to certain embodiments, internal surface 948 is secured to external surface 950 substantially over its entire surface. It will be recognized that any number of methods may be used to secure internal surface 948 of sleeve 940 to external surface 916 of spout 910. For example, sleeve 940 may be made separately from spout 910, and then assembled on spout 910 and joined thereto with an adhesive, for example. Alternatively, sleeve 940 may be molded on external surface 916 of spout 910. To facilitate the molding process, surface 916 of spout 910 may be roughened to facilitate better connection between surface 948 and surface 916.

The distance between internal surface 948 and external surface 950 of wall 942 may vary so that the external surface 950 defines a plurality of protrusions 952 and a plurality of troughs 954. Protrusions 952 have free ends 956 that cooperate with surface 522 of wall 520 of fluid port 500 to limit passage of fluids. Each protrusion 952 encircles the spout 910.

The profile of external surface 950 may vary, such that the shape of protrusions 952 may vary as a consequence. Where external surface 950 has a sinusoidal profile, similar to that illustrated, protrusions 952 and troughs 954 may have a substantially semi-circular profile when viewed in cross-section, although the relative dimensions may vary. Alternatively, a square-wave or triangular-wave profile may be used, with a consequential effect on the shape of protrusions 952 and troughs 954. For that matter, different shapes may be used for protrusions 952 and for troughs 954.

In operation, as seen in FIG. 14, end 932 of spout 910 is spaced from first end 524 of adapter 500 because of the cooperation between container 902 and shoulder 536. Adapter 900 is disposed into the space with protrusions 952 abutting surface 522 in region 530. The cooperation of protrusions 952 with surface 522 causes a plurality of spaces 960 to be defined between adjacent protrusions 952, and limits the passage of fluid from space.

Figure 15:
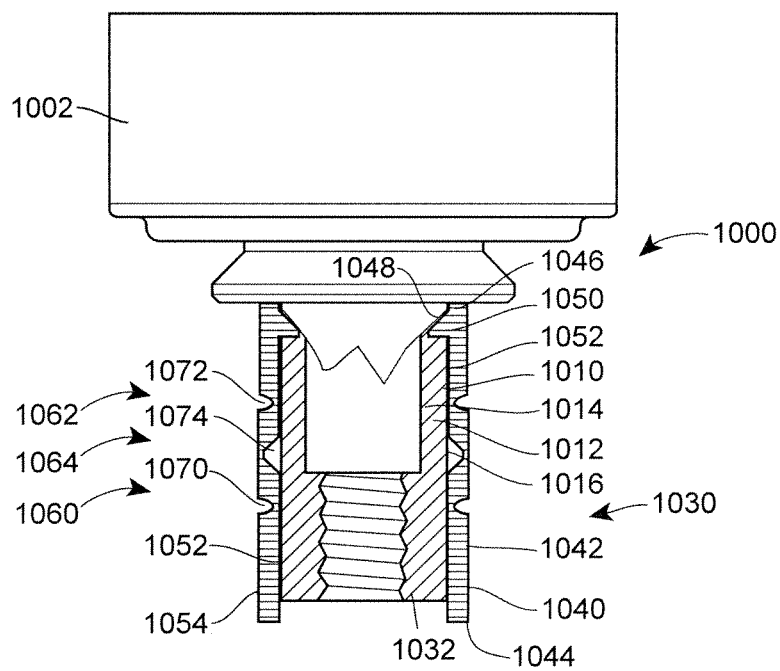
FIG. 15 is a cross-sectional view of an adapter attached to a container spout.
Figure 16:
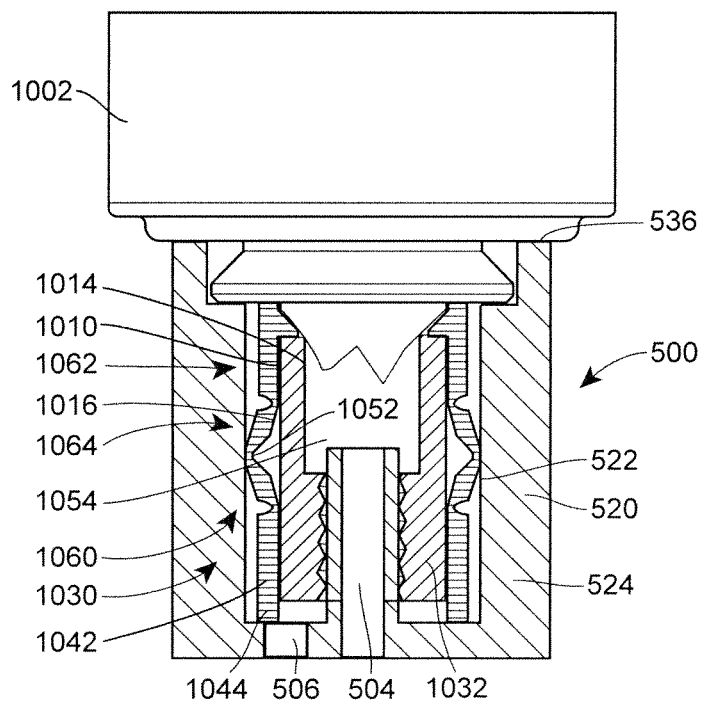
FIG. 16 is a cross-sectional view of the adapter of FIG. 15 in combination with a vaporizer fluid port.

As illustrated in FIGS. 15 and 16, adapter 1000 also includes seal 1030 in the form of sleeve 1040 disposed about spout 1010. However, unlike sleeve 940, sleeve 1040 is not intended to be secured substantially over its entire surface to external surface 1016 of spout 1010. Instead, sleeve 1040 is intended to move in part relative to spout 1010 to limit the passage of fluid.

Turning first to FIG. 15, sleeve 1040 includes wall 1042 having first end 1044 and second end 1046. First end 1044 of wall 1042 depends beyond end 1032 of spout 1010, and is moveable relative to spout 1010. Second end 1046 of wall 1042 is coupled to external surface 1016 of spout 1010. In particular, triangular cross-section groove 1048 is defined in external surface 1016 of wall 1012 of spout 1010. Second end 1046 of wall 1042 has complementary triangular cross-section ridge 1050 defined on internal surface 1052 of wall 1042 depending radially inward. Ridge 1050 is disposed within and cooperates with groove 1048 to couple sleeve 1040 to external surface 1016 of spout 1010. An adhesive may also be used to secure ridge 1050 to wall 1012.

Wall 1042 of sleeve 1040 does not have a uniform thickness along its length between first and second ends 1044, 1046. Rather, the distance between internal surface 1052 and external surface 1054 varies, with the distance (or thickness) being smallest between internal and external surfaces 1052, 1054 in three regions 1060, 1062, 1064. It will be recognized that wall 1042 is more likely to bend at these regions 1060, 1062, 1064 than at other regions along the length of wall 1042, given a similar material used to form the entirety of wall 1042. In fact, it may be said that regions 1060, 1062, 1064 form three living hinges along the length of wall 1042. Moreover, these changes in thickness alternate along the length of the wall, such that wall 1042 has troughs 1070, 1072 defined in external surface 1054 in regions 1060, 1062, and has trough 1074 defined in internal surface 1052 in region 1064.

In operation, as illustrated in FIG. 16, adapter 1000 is received with passage 1014 defined by spout 1010 in fluid communication with openings 506 and a valve assembly (not shown) in fluid communication with passage 504, so that fluid communication is established between container 1002 and fluid port 500. Again, adapter 1000 is advanced into the space until container 1002 abuts shoulder 536 of wall 520. As adapter 1000 is advanced, end 1044 of seal 1030 contacts first end 524 of port 500. The cooperation of end 1044 and first end 524 may limit the passage of fluid.

In addition, end 1044 of seal 1030 is moved in the direction of end 1032 of spout 1010, such that the distance between end 1044 and end 1032 in this engaged state is smaller than the distance between end 1044 and end 1032 in a disengaged state. The cooperation of end 1044 and first end 524 causes bending of wall 1042 in regions 1060, 1062, 1064, thereby spacing the internal surface 1052 of sleeve 1040 from external surface 1016 of spout 1010. Additionally, the bending of wall 1042 may cause external surface 1054 of wall 1042 in region 1064 to abut surface 522 of wall 520 in region 530. This cooperation between external surface 1054 of wall 1042 and surface 522 of wall 520 also may limit passage of fluid.

FIGS. 17-21 and 22A-C illustrate an embodiment similar to the embodiment of FIGS. 1A-C, 2 and 3 in that an adapter assembly is attached to a vaporizer fluid port assembly, rather than the container spout, as in the embodiments illustrated in FIGS. 4-16. However, unlike the preceding embodiments, the vaporizer fluid port assembly illustrated in FIGS. 17-21 and 22A-C is configured for a different anesthetic vaporizer. Nevertheless, while the structure of the adapter may vary, the adapter assembly of FIGS. 17-21 and 22A-C and the adapter of FIGS. 1A-C, 2 and 3 dispose a seal at a particular location within a passage in a vaporizer fluid port.

Figure 17:
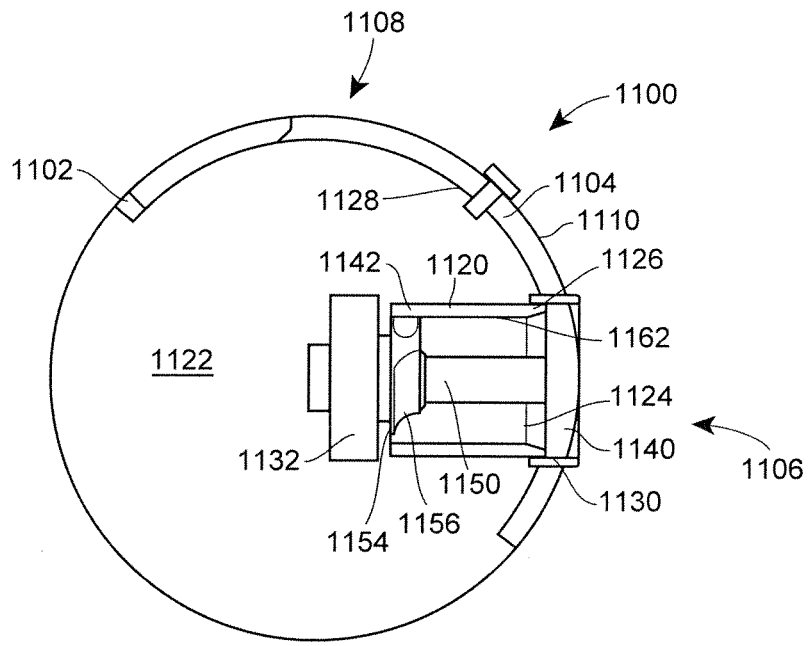
FIG. 17 is a side view of a vaporizer fluid port assembly in an extended, or closed, state.

Referring first to FIG. 17, vaporizer fluid port assembly 1100 is illustrated, of the general type manufactured and sold by GE Medical. Fluid port assembly 1100 includes wall 1102, of which only a fragment may be illustrated in FIGS. 17-21 and 22A-C. It will be recognized that wall 1102 is arcuate in shape in the actual device, and thus extends through less than 360 degrees. In fact, it will be recognized that much of the structure of a fluid port of a conventional GE vaporizer fluid port has been removed to expose certain elements discussed herein. This has been done to simplify the discussion, rather than with an intent to eliminate elements of the conventional device.

Wall 1102 as a first elongated slot 1104 formed therein. Slot 1104 extends from a first end 1106 into which a container spout may be advanced (see FIG. 22A) or retracted to a second end 1108 in which the motion of the spout towards or away from the slot is limited (see FIG. 22C). For example, the slot 1104 may have edges 1110 (only one of which is shown in FIG. 17) that cooperate with a locking rim of the spout to limit the separation of the spout from the port assembly 1100 at the second end 1108 of the slot 1104. To this end, the spacing of the edges 1110 of the slot 1104 may be greater proximate to the first end 1106 than the spacing of the edges 1110 proximate to the second end 1108.

Fluid port assembly 1100 may also include conduit 1120. Conduit 1120 is disposed within space 1122 bounded by wall 1102, and has passage 1124 aligned with slot 1104 (see also FIG. 17). Conduit 1120 has end 1126 that is spaced from inner surface 1128 of wall 1102, and is supported relative to wall 1102 to maintain this spacing.

Fluid port assembly 1100 may include two elements that move relative to wall 1102 and conduit 1120: first element 1130 and second element 1132. First element 1130 is disposed proximate to end 1126 of conduit 1120, and has passage 1140 therethrough in which conduit 1120 is received. Second element 1132 is disposed proximate to end 1142 of conduit 1120. Second element 1132 has stem-like post 1150 with a passage 1152 therethrough (see FIG. 19), the stem-like post 1150 depending from a cylindrical base 1154 with an annular groove 1156 that extends about the perimeter of the base 1154.

First element 1130 moves separately from second element 1132. First element 1130 is biased toward the extended state illustrated in FIG. 17 by a biasing element (not shown), such as a coil spring. First element 1130 cooperates with the rim of the spout to force the rim up against wall 1102, and in particular spaced edges 1110 of slot 1104. The cooperation of the rim of the spout and wall 1102 limits separation of the spout and associated container from fluid port assembly 1100.

Second element 1132 cooperates with a valve assembly of the anesthetic container to permit liquid anesthetic to enter the fluid port assembly 1102 and to permit gaseous return to the container. In particular, with the element 1132 in the extended, or closed, state illustrated in FIG. 17, the wall of the conduit 1120 limits the passage of liquid anesthetic from the container into the vaporizer. However, the element 1132 may be moved from the position illustrated in FIG. 17 to that illustrated in FIG. 22C through cooperation of the spout and second cylindrical piece 1132. In the retracted, or open, state of FIG. 22C, liquid anesthetic may pass through conduit 1120 and around piece 1132 through groove 1156. Gaseous anesthetic from the vaporizer returns along stein 1150, and in particular passage 1152, which is in fluid communication with a valve assembly (not shown) disposed in the anesthetic container spout.

Figure 18:
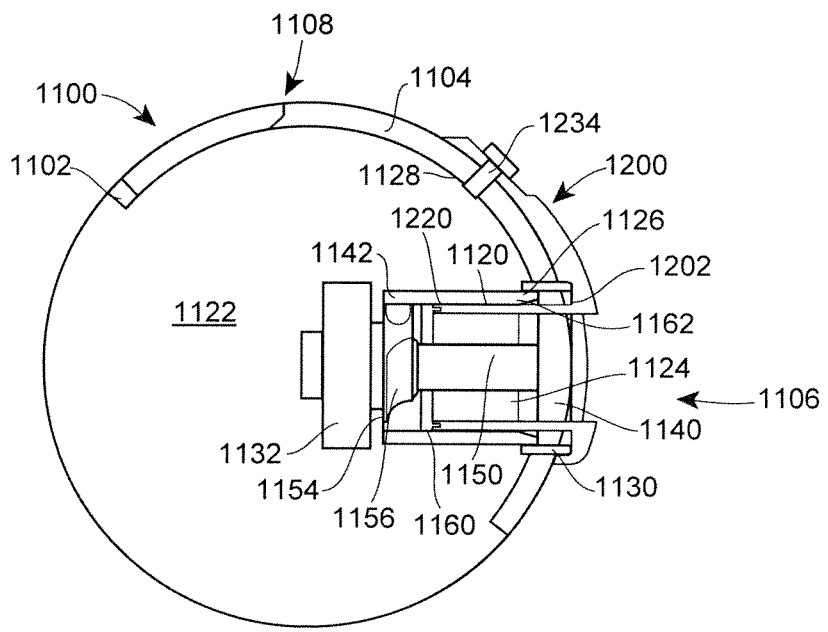
FIG. 18 is a side view of the vaporizer fluid port assembly of FIG. 17 in combination with an adapter assembly according to a further embodiment of the present disclosure.

Referring now to FIG. 18, seal 1160 is disposed in conduit 1120 between ends 1126, 1142. Seal 1160 abuts inner surface 1162 of conduit 1120, and abuts an outer surface of a container spout as the container spout is advanced into conduit 1120 (see FIGS. 22A-C). As illustrated in FIG. 18, adapter 1200 is attached to port 1100 to dispose seal 1160 at the desired location along conduit 1120.

Figure 19:
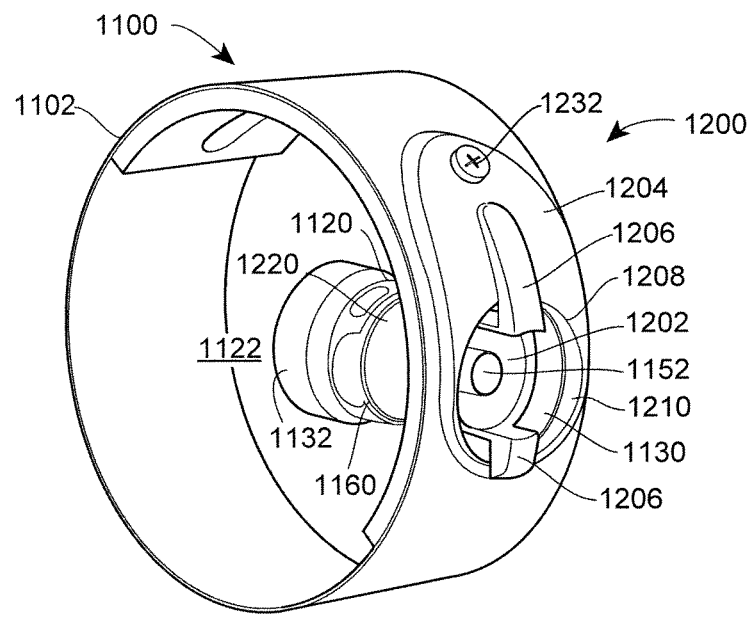
FIG. 19 is a perspective view of the combination of FIG. 18.
Figure 20:
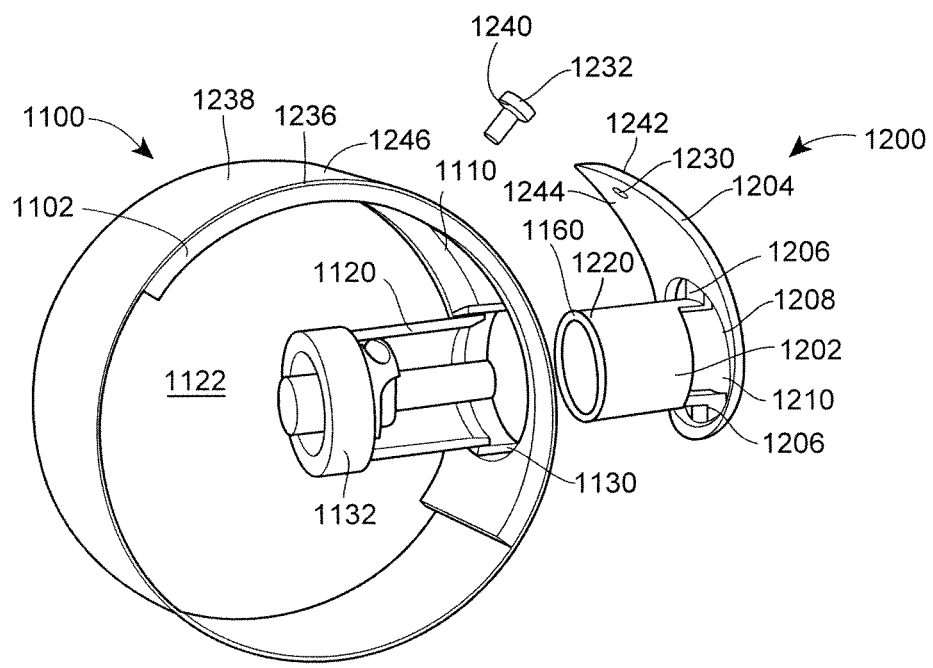
FIG. 20 is an exploded, perspective view of the combination of FIG. 18.

Turning next to FIGS. 19 and 20, the adapter assembly 1200 includes conduit 1202 and attachment tab 1204. As illustrated, conduit 1202 is formed integrally with attachment tab 1204. According to other embodiments, conduit 1202 and tab 1204 may be made separately, and later joined together to define adapter 1200. Conduit 1202 is joined to tab 1204 by a plurality of spacers 1206, which join conduit 1202 to tab 1204 and position conduit 1202 relative to opening 1208 in tab 1204. While two spacers 1206 are illustrated, it will be recognized that only one spacer 1206 may be used, or a greater number of spacers 1206 may be used. Spacers 1206 also define spaces 1210, through which portions of a rim of a container spout will be disposed to act against edges 1110 between the positions illustrated in FIGS. 22A and 22B.

The conduit 1202 may have a groove (see, e.g., FIG. 18) formed at end 1220 in which a portion of seal 1160 is received. The receipt of a portion of seal 1160 into the groove of conduit 1202 attaches seal 1160 to conduit 1202. As was the case above, seal 1160 may be integrally-molded with adapter 1200, and conduit 1202 in particular.

Attachment tab 1204 may have opening 1230 formed therethrough to receive fastener 1232. Fastener 1232 may be disposed through opening 1230 and into opening 1234 formed in wall 1236 of plate 1238. Plate 1238 is disposed over slot 1104 in wall 1102 of fluid port assembly 1100. As shown, plate 1238 is annular, and depends entirely about wall 1102 of fluid port assembly 1100; according to other embodiments, plate 1238 may only extend over a portion of the wall 1102, such that plate 1238 is arcuate instead of annular. Fastener 1232 may be threaded and may be received in a threaded stud (not shown), which stud is moveable with the conduit 1120 from the position in FIG. 22A to that shown in 22C.

With fastener 1232 secured to the stud, surface 1240 of fastener 1232 faces surface 1242 of attachment tab 1204 to limit movement of tab 1204 relative to wall 1236. At the same time, surface 1244 of tab 1204 abuts surface 1246 of wall 1236; to this end, where the wall 1236 is annular or arcuate, tab 1204 and wall 1236 may have similar curvatures.

As mentioned above, fastener 1232 may be a threaded fastener, and thus may be threaded to be receive the stud (not shown). It will be recognized that fastener 1232 need not be threaded according to all embodiments according to the present disclosure, such as variants of the vaporizer that do not include the threaded stud.

Also, it will be recognized that, as illustrated, fastener 1232 depends into slot 1104. As such, if adapter assembly 1200 were to be used with certain fluid port assemblies, then when the spout is advanced from the position illustrated in FIG. 22A towards that of FIG. 22C, fastener 1232 would first abut with second end 1108 of slot 1104, and thus limit the movement of the spout between the state illustrated in FIG. 22A and that of FIG. 22C. According to the illustrated embodiment, a slot 1260 is formed in wall 1102 of the fluid port assembly 1100. When the spout is moved from the position of FIG. 22A to that of FIG. 22C, fastener 1232 moves first along slot 1104 and then along slot 1260.

Figure 21:
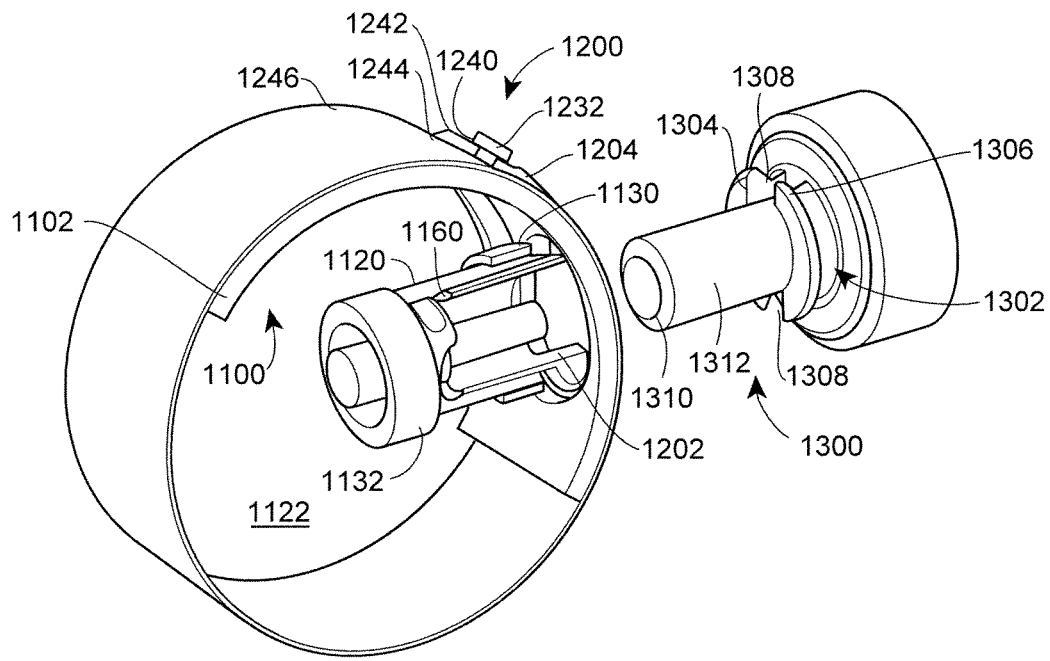
FIG. 21 is a perspective view of the combination of FIG. 18 and a spout of an anesthetic container.

The cooperation of the fluid port assembly 1100, adapter assembly 1200 and an anesthetic container spout 1300 in operation is now discussed with reference to FIGS. 21 and 22A-C. As illustrated in FIG. 21, spout 1300 has rim 1302 with first section 1304 and second section 1306 separated from each other by spaces 1308. Spaces 1308 receive spacers 1206 that connect the conduit 1202 to the attachment tab 1204, and thus the size and number of spaces 1308 depends on the size and number of spacers 1206, and vice versa.

Figure 22A:
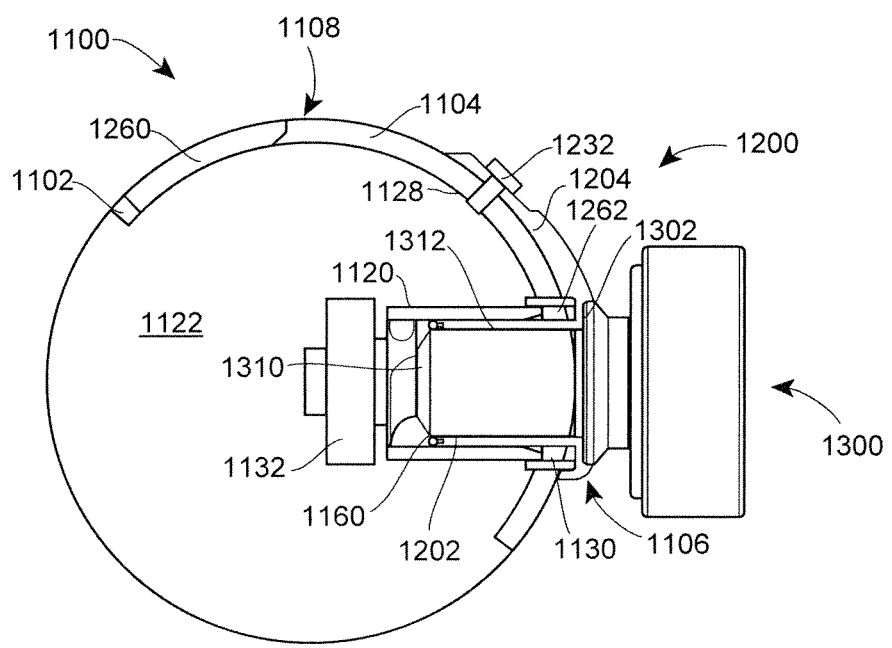
FIG. 22A is a side view of the combination of FIG. 18 with the anesthetic container spout advanced into the adapter assembly and the fluid port in the closed state.

As shown in FIG. 22A, spout 1300 is advanced into conduit 1202 through aperture 1262 in wall 1236 of the plate 1238 and opening 1208 in attachment tab 1204. End 1310 of spout 1300 abuts a surface of element 1132. Additionally, outer surface 1312 abuts inner surface of seal 1160. Seal 1160 limits passage of fluid or gaseous anesthetic from the fluid port assembly 1100.

Figure 22B:
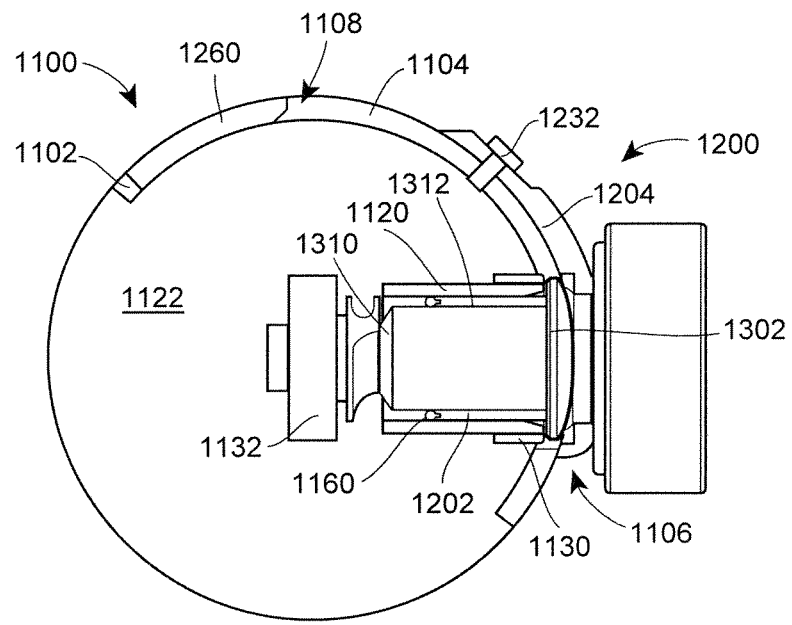
FIG. 22B is a side view of the combination of FIG. 18 with the anesthetic container spout further advanced into the adapter assembly and the fluid port in an intermediate state.

From the position in FIG. 22A, spout 1300 is further advanced into the conduit 1120 of fluid port assembly 1100, as illustrated in FIG. 22B. With end 1310 of spout 1300 abutting element 1132, element 1132 is moved from the extended state to the retracted state, which may permit liquid anesthetic to pass from the container, along passage 1124 of conduit 1106, through groove 1156 of element 1132, and into the vaporizer.

Figure 22C:
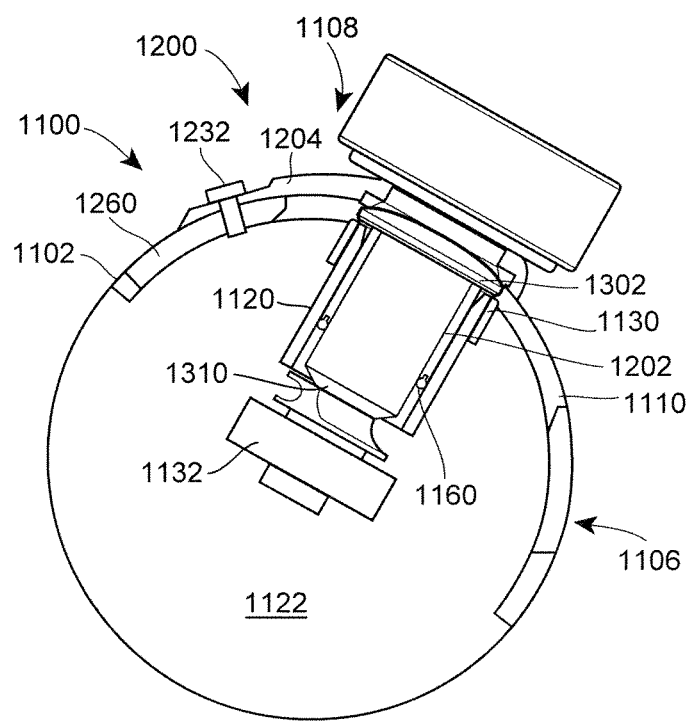
FIG. 22C is a side view of the combination of FIG. 18 with the anesthetic container spout advanced into the adapter assembly, the fluid port in the open state, and the anesthetic container spout advanced along an elongated slot formed in a wall of the vaporizer fluid port assembly.

Spout 1300 is then moved upward, from the position in FIG. 22B to that of FIG. 22C. As spout 1300 is moved upward, rim 1302 of spout 1300 cooperates with edges 1110 of wall 1102 of fluid port assembly 1100 to limit movement of spout 1300 away from fluid port assembly 1100. Additionally, plate 1238 covers slot 1104 in wall 1102, both in the direction of the advance of spout 1300 as well as over the path spout 1300 has already traversed. Further, liquid anesthetic passes from the container, along passage 1124 of conduit 1106, through groove 1156 of element 1132, and into the vaporizer.

What is claimed is:

1. An adapter for establishing fluid communication between an anesthetic agent container and an anesthetic vaporizer, the adapter comprising:
    a spout having an internal passage therethrough for receiving a stem-like conduit, and an external surface, the spout having a first end and a second end; and
    a seal comprising a sleeve, the sleeve having a sleeve internal surface disposed about the external surface of the spout,
    the sleeve having a first end and a second end coupled to the external surface of the spout,
    the first end depending a first distance longitudinally beyond the first end of the spout in a first, disengaged state, and the first end depending a second distance smaller than the first distance longitudinally beyond the first end of the spout in a second, engaged state, the sleeve internal surface spaced in part from the external surface of the spout in the engaged state,
    wherein in the second, engaged state, the sleeve is adapted to contact an inner surface of vaporizer port of the anesthetic vaporizer to limit the passage of fluid therebetween.

2. The adapter according to claim 1, the sleeve comprising at least one living hinge, the sleeve bending at the living hinge in the second, engaged state.

3. The adapter according to claim 1, the sleeve having a region of reduced thickness, the sleeve bending at the region of reduced thickness in the second, engaged state.

4. The adapter according to claim 3, the sleeve having at least three regions of reduced thickness, the sleeve bending at the at least three regions of reduced thickness in the second, engaged state.

5. The adapter according to claim 1, wherein the second end of the spout has a recess defined in the external surface and the second end of the sleeve has a ridge depending radially inward, the ridge disposed within the groove to couple the second end of the spout to the second end of the sleeve.

* * * * *